US 8,226,719 B2
Jul. 24, 2012

(12) United States Patent
Melsheimer et al.

(54) METHOD AND BONE CEMENT SUBSTITUTE KIT FOR STABILIZING A COLLAPSED VERTEBRA OF A PATIENT

(75) Inventors: Jeffry S. Melsheimer, Springville, IN (US); Nathaniel A. Irwin, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1287 days.

(21) Appl. No.: 11/939,572

(22) Filed: Nov. 14, 2007

(65) Prior Publication Data
US 2009/0125031 A1 May 14, 2009

(51) Int. Cl.
*A61F 2/44* (2006.01)
*A61B 17/20* (2006.01)
(52) U.S. Cl. ...... 623/17.12; 623/17.11; 606/92
(58) Field of Classification Search ........ 606/86 R, 606/92–94, 279; 623/17.11–17.16; 128/200.14, 128/200.25, 201.21
See application file for complete search history.

(56) References Cited

U.S. PATENT DOCUMENTS

| 6,005,163 | A | * | 12/1999 | Tepic | 128/898 |
|---|---|---|---|---|---|
| 6,425,949 | B1 | | 7/2002 | Lemaitre et al. | |
| 2004/0048947 | A1 | | 3/2004 | Lidgren et al. | |
| 2005/0070913 | A1 | * | 3/2005 | Milbocker et al. | 606/92 |
| 2006/0079905 | A1 | * | 4/2006 | Beyar et al. | 606/76 |
| 2006/0082168 | A1 | * | 4/2006 | Joosten et al. | 293/102 |
| 2006/0096504 | A1 | | 5/2006 | Grover et al. | |
| 2006/0122623 | A1 | * | 6/2006 | Truckai et al. | 606/94 |
| 2006/0149379 | A1 | * | 7/2006 | Kuslich et al. | 623/17.12 |
| 2006/0173464 | A1 | | 8/2006 | Ellman et al. | |
| 2006/0182779 | A1 | * | 8/2006 | Brandom et al. | 424/423 |
| 2007/0128248 | A1 | | 6/2007 | Moseley et al. | |
| 2007/0255406 | A1 | * | 11/2007 | Trieu | 623/17.11 |

* cited by examiner

*Primary Examiner* — Thomas Barrett
*Assistant Examiner* — Matthew Lawson
(74) *Attorney, Agent, or Firm* — Woodard, Emhardt, Moriarty, McNett & Henry LLP

(57) ABSTRACT

In at least one embodiment of the present invention, a method for stabilizing a collapsed vertebra of a patient is provided. The method comprises introducing a supercooled liquid into the collapsed vertebra. A solid structure that supports the collapsed vertebra is then form by solidifying the supercooled liquid.

23 Claims, 3 Drawing Sheets

METHOD AND BONE CEMENT SUBSTITUTE KIT FOR STABILIZING A COLLAPSED VERTEBRA OF A PATIENT

BACKGROUND OF THE INVENTION

1. Field of the Invention

The present invention relates to a method for using novel bone cements and bone cement substitute kits.

2. Background

There is a clinical need to fill defects in vertebra, such as for patients suffering from severe back pain caused by osteoporosis, metastatic tumours or back injuries. Currently, these defects can be repaired by using bone cements that can be molded and subsequently cured via a chemical reaction.

The most widely used bone cements are based on polymethylmethacrylate (PMMA) and hydroxyapatite. These have good strength characteristics but also have a number of drawbacks. These cement systems are a two-part thermosetting polymer that have approximately five to ten minutes of working time once the components are mixed. As for example with the PMMA based system, one of the components is a liquid monomer, methylmethacrylate, which is noxious and toxic to tissues. The other component, the polymer component, is a powder that can be difficult to mix thoroughly. Moreover, the viscosity of the cement constantly increases after mixing and may require very high pressures to inject the cement into the vertebra especially near the end of the cement's working time and/or a large bore needle may be necessary for the injection.

Accordingly, there remains a need in the art for a bone cement which has ease of handling, including flexible working times with suitable injection-ability into a vertebra before setting up and becoming a solid.

BRIEF SUMMARY OF THE INVENTION

In at least one embodiment of the present invention, a method for stabilizing a collapsed vertebra of a patient is provided. The method comprises introducing a supercooled liquid into the collapsed vertebra. A solid structure that supports the collapsed vertebra is then form by solidifying the supercooled liquid.

In at least one other embodiment of the present invention, the method comprises inserting a needle into the collapsed vertebra. A supercooled liquid is introduced from the needle and into the collapsed vertebra. At least a portion of the collapsed vertebra is filled with the supercooled liquid. The supercooled liquid is then solidified to form a solid structure that supports the collapsed vertebra.

In at least another embodiment of the present invention, a cement substitute kit for stabilizing a collapsed vertebra of a patient is provided. The kit comprises one of a supercooled liquid and a precursor of the supercooled liquid. A syringe which includes a plunger is configured for dispensing the supercooled liquid from the syringe when it is actuated by an interventionalist. A needle is configured for advancing the supercooled liquid into the collapsed vertebra. The kit further comprises one of a seed crystal, an electrical charge device and/or an energy impulse device for solidifying the supercooled liquid within the collapsed vertebra.

Further objects, features and advantages of the invention will become apparent from consideration of the following description and the appended claims when taken in connection with the accompanying drawings.

BRIEF DESCRIPTION OF THE DRAWINGS

FIG. 2b is an exploded view of FIG. 2a;

DETAILED DESCRIPTION OF THE INVENTION

Detailed embodiments of the present invention are disclosed herein. It is understood however, that the disclosed embodiments are merely exemplary of the invention and may be embodied in various and alternative forms. The figures are not necessarily to scale; some figures may be exaggerated or minimized to show the details of a particular component. Therefore, specific structural and functional details disclosed herein are not to be interpreted as limiting, but merely as a representative basis for the claims and for teaching one skilled in the art to practice the present invention.

Examples of the present invention seek to overcome some of the concerns associated with stabilizing a collapsed vertebra of a patient with bone cement while minimizing toxic effects to the patient's body and enhancing ease of handling of the cement for introduction into the collapsed vertebra.

Employing the principles of the present invention is, for example, a method and a kit for stabilizing the collapsed vertebra using bone cement comprising a supercooled liquid. A supercooled liquid is a material in a liquid phase having a temperature below its freezing point. The supercooled liquid generally lacks a nucleation center or the onset of nucleation as the liquid material is decreased in temperature below its freezing point and thus, remains in the liquid phase without undergoing a phase-change to a form a solid. However, upon introduction of a seed crystal (a nucleating crystal from which a larger crystal or crystals can be grown), an energy impulse or a light electrical charge, the supercooled liquid transitions to the solid phase of the material. This liquid-solid phase transition caused by nucleation of the supercooled liquid typically occurs quite rapidly to form a solid structure.

The supercooled liquid, which is preferably a biocompatible solution with a relatively low and stable viscosity, may be easily introduced into the fractured vertebra, such as for example, by a needle or some other form of cannula, without substantially limiting the work time before solidifying. This allows the interventionalist sufficient time to fill and monitor the filling of the collapsed vertebra, without the use of higher injection pressures, larger bone cement injection needles or incomplete filling of the vertebra due to premature curing of the bone cement. Once the collapsed vertebra is filled, the supercooled liquid is solidified to form a structure within the collapsed vertebra stabilizing the vertebra.

Figure 1:
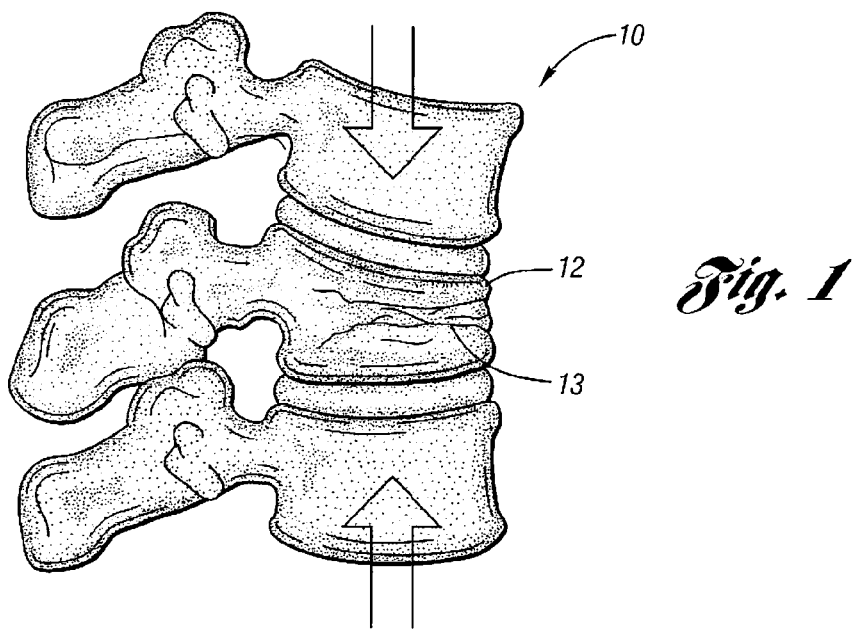
FIG. 1 is a perspective view of a collapsed vertebra.

Referring now to the drawings, FIG. 1 illustrates vertebrae 10 which includes a collapsed vertebra 12 with a compression fracture 13. The vertebra 10 may be for example in the thoracic or lower spine of the patient. In the compression fracture 13 of the vertebra 12, the bone tissue of the verebral body collapses. This condition is commonly caused by osteoporosis and less often by a tumor, or trauma to the back.

Figure 2A:
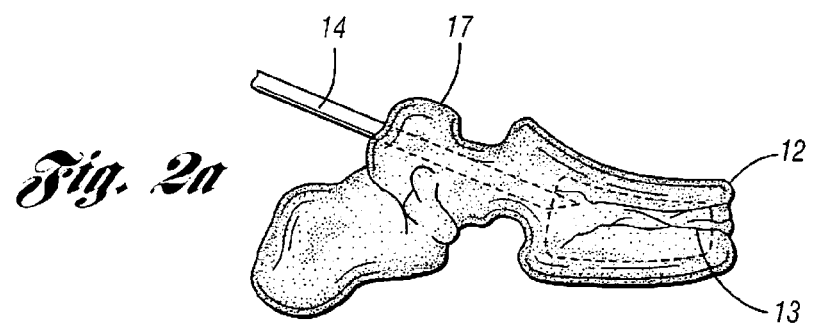
FIG. 2a is a partial side view of an embodiment for stabilizing a collapsed vertebra in accordance with one example of the present invention.
Figure 2B:
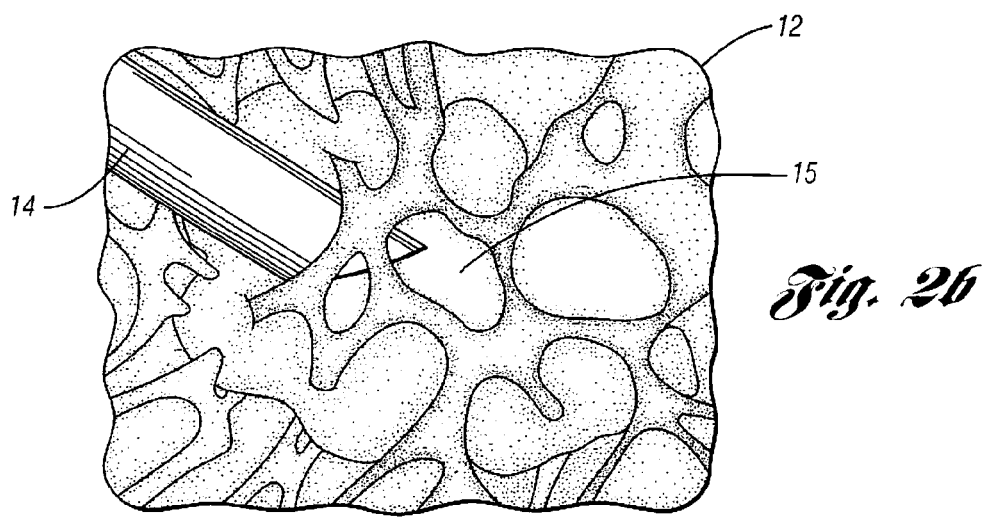
Figure 2C:
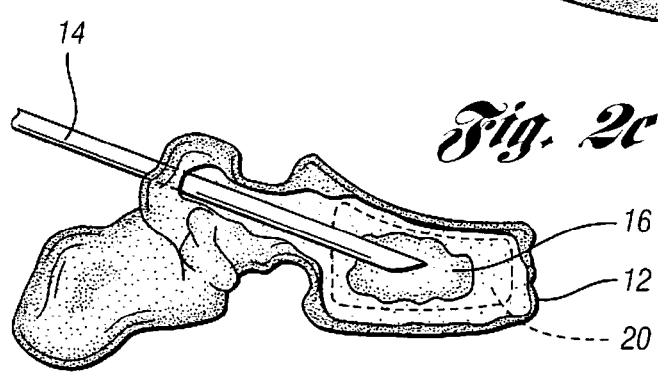
FIG. 2c is a partial side view of another embodiment for stabilizing a collapsed vertebra in accordance with one example of the present invention.

Referring now to FIGS. 2a, 2b and 2c, examples of at least one embodiment of the present invention are provided. The collapsed vertebra 12 may be stabilized by either vertebroplasty or kyphoplasty, both of which are medical procedures for introducing bone cement into the collapsed vertebra. These procedures stabilize the collapsed vertebra by filling in open spaces within the vertebra 12 to provide a more continuous and solid form. Kyphoplasty may further stabilize the vertebra 12 by restoring vertebral spacing which alleviates nerve pinching about the vertebra 12. It should be noted that the present invention applies to both medical procedures despite many of the various embodiments discussed herein are described using vertebroplasty.

Vertebroplasty requires a patient to lie on their stomach throughout the entire procedure. It is performed under a local anesthesia and/or a light sedative. A small nick is then made in the skin near the spine and a needle 14 is inserted percutaneously. As illustrated in FIG. 2b, the needle 14 may be inserted into the interior 15 of the vertebra 12, for example via or through the left or right pedicle 17 of the vertebra 12.

In one example a supercooled liquid 16 is introduced into the collapsed vertebra 12, preferably via the needle 14. At least a portion of the collapsed vertebra 12 is filled with the supercooled liquid 16.

In at least one embodiment, the supercooled liquid 16 is an aqueous solution with a relatively low viscosity similar to water. The supercooled liquid 16 may comprise sodium acetate, sodium acetate trihydrate, sodium sulphate, hydrated forms of sodium sulphate called Glauber's salt, various organic and/or eutectic salts, or mixtures thereof. Other suitable compounds or solutions known to those skilled in the art may also be used which have a propensity to remain in a liquid phase below their freezing point whereupon a phase-change to a solid may be induced by introducing a seed crystal, an energy impulse or some other form of nucleating mechanism.

The supercooled liquid 16 may also include a thickener for adjusting the viscosity of the supercooled liquid 16. For example, if the supercooled liquid 16 is an aqueous solution with a viscosity between about 0.5 to 10 centipoise (cps), it may be desirable to add a thickener to increase the viscosity to between about 10 to 1000 cps to facilitate filling of the collapsed vertebra 12 without substantial leakage of the supercooled liquid 16 through the compression fracture 13 and into an area outside of the collapsed vertebra 12.

The thickener may also be added to the supercooled liquid 12 during introduction into the collapsed vertebra or pre-mixed into the supercooled liquid prior to introduction into the collapsed vertebra. In the pre-mixed scenario, the thickener may be added directly to the supercooled liquid or alternatively, the thickener may be incorporated into a precursor of the supercooled liquid. A precursor of the supercooled liquid may be the material in a liquid phase at a temperature above its freezing point or the material in a solid phase below its freezing point, which if heated above its freezing point transitions into the liquid phase and further, when the liquid phase is cooled below its freezing point, the material remains in the liquid phase to form the supercooled liquid. To further illustrate, sodium acetate trihydrate has a freezing point of about 58 Celsius (C) and is a supercooled liquid when it is in a liquid phase at a temperature below about 58 C. Alternatively, sodium acetate trihydrate may be a precursor of a supercooled liquid if it is in a solid phase below about 58 C or in a liquid phase above about 58 C.

Suitable commercially available thickener may be used which preferably do not induce premature nucleation of the supercooled liquid. Moreover, the thickener may be a radiopacifier, such as for example, barium sulphate, zirconium dioxide and/or micronized tantalum. The radiopacifier may also serve the purpose of allowing the collapsed vertebra 12 to be monitored, via fluoroscopy for example, during filling with the supercooled liquid. Accordingly, the interventionalist may assess and adjust contemporaneously the amount of supercooled liquid being introduced into the collapsed vertebra 12.

Figure 3:
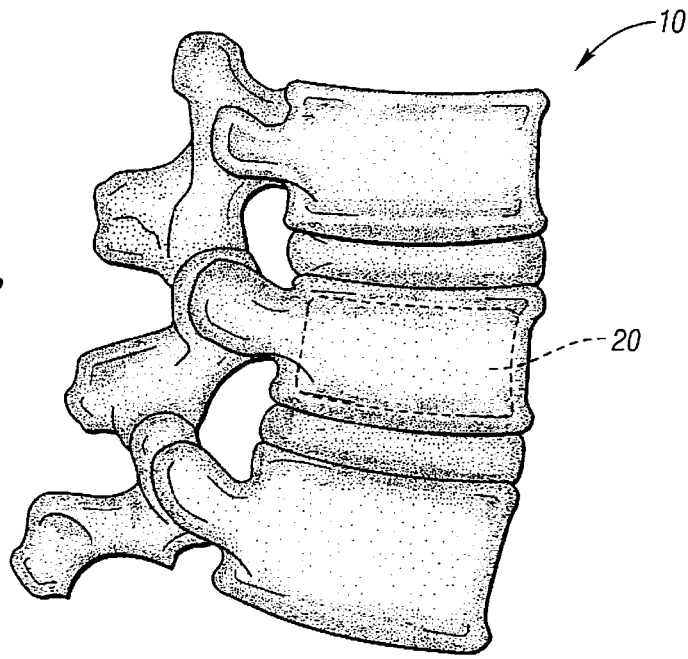
FIG. 3 is a partial side view of a stabilized collapsed vertebra in accordance with one example of the present invention.

Referring to FIG. 2c and FIG. 3, the supercooled liquid 16 is solidified to form a structure 20 that supports the collapsed vertebra 12. The supercooled liquid 16 may be solidified for example by introducing a seed crystal. A seed crystal may be a crystal formed of the same material as the supercooled liquid 16. For example, if the supercooled liquid 16 comprises sodium acetate trihydrate, a crystal (seed crystal) of sodium acetate trihydrate (a white non-toxic powder) may be introduced to the supercooled liquid 16. The supercooled liquid 16 will immediately begin to solidify about the sodium acetate trihydrate crystal. Alternatively, the seed crystal may be a material formed of a different material than the supercooled liquid 16 providing either a chemical or physical nucleating site. For example, a crystal of sodium acetate may be added to a supercooled liquid 16 of sodium acetate trihydrate to form a chemical nucleation site which results from the similar chemistries and chemical attraction between the seed crystal and the supercooled liquid 16. In yet another example, an inorganic salt crystal may be added to the supercooled liquid 16 which forms a physical nucleation site that promotes crystallization of the supercooled liquid 16 by providing a shaped surface for crystal formation and growth.

The seed crystal may be introduced to the supercooled liquid 16 via the needle 14 or another suitable insertion device. Moreover, the seed crystal may be placed into the supercooled liquid 16 subsequent to the liquid 16 being introduced into the collapsed vertebra 12 or alternatively, the seed crystal may be placed into the collapsed vertebra 12 followed by introduction of the supercooled liquid 16 into the vertebra 12. This latter scenario may produce an immediate solidification of the structure 20 as the collapsed vertebra 12 is being filled with the supercooled liquid 16.

The supercooled liquid 16 may also be solidified by applying an energy impulse or an electric charge to the supercooled liquid 16. For example, a light electrical charge may be provided to the supercooled liquid via an electrode or electrical transducer introduced into the supercooled liquid 16 via the needle 14. Alternatively, an energy impulse may be introduced into the supercooled liquid 16 by an ultrasonic head, ultrasonic transducer or some other device capable of providing an energy impulse. Such energy impulses and/or electrical charges initiate nucleation causing a phase transition to take place in the supercooled liquid 16. Other suitable means known in the art for nucleating a supercooled liquid 16 may also be used.

In at least one embodiment, the supercooled 16 liquid solidifies to form the structure 20 by crystallizing which generates an exothermic liquid to solid phase-change. The heat emitted from the exothermic phase-change is preferably at a temperature that provides the patient with some pain relief in the area of the collapsed vertebra 12. Moreover, the phase-change generally occurs quickly and may form the structure 20 within about 60 seconds and more preferably within about 30 seconds.

The stabilizing structure 20 may be formed within and/or about the collapsed vertebra 12 and may help restore vertebral spacing and alleviate nerve pinching by supporting the collapsed vertebra 12 generally in at least a compressive mode. Preferably, the structure substantially fills in the open spaces 15 of the collapsed vertebra 12 providing a more dense and continuous vertebra which enhances mobility of the patient.

In at least one embodiment, the supercooled liquid 16 is provided with reinforcing means for improving the fracture toughness and strength of the resulting solid structure 20. Various reinforcing material may be incorporated into the supercooled liquid 16 and/or the precursor of the supercooled liquid and include conventional fiber materials such as glass, carbon or alumina fiber, Nitinol alloys (porous NiTi alloys), small intestine submucosa (SIS gel), thermoplastic fiber, whiskers, nano-fillers, inorganic and/or organic fillers, commercially available toughening agents, thermoplastic fillers, elastomeric and rubber additives, and clay.

In at least one other embodiment, the supercooled liquid 16 may form the solid structure 20 which is at least partially soluble in water, blood and/or other body fluids. To prevent or retard dissolution of the structure 20 over prolonged exposure to body fluids, the supercooled liquid 16 may be microencapsulated within membranes which are substantially impermeable to aqueous body fluids. The membranes are preferable made of a polymer that is impermeable to water, such as for example polyethylene terephthalate (PET) or polybutylene terephthalate (PBT). Other suitable membranes may also be used. The microencapsulated supercooled liquid may be introduced into the collapsed vertebra 12 and solidified by any of the means discussed in the preceding paragraphs.

Figure 4:
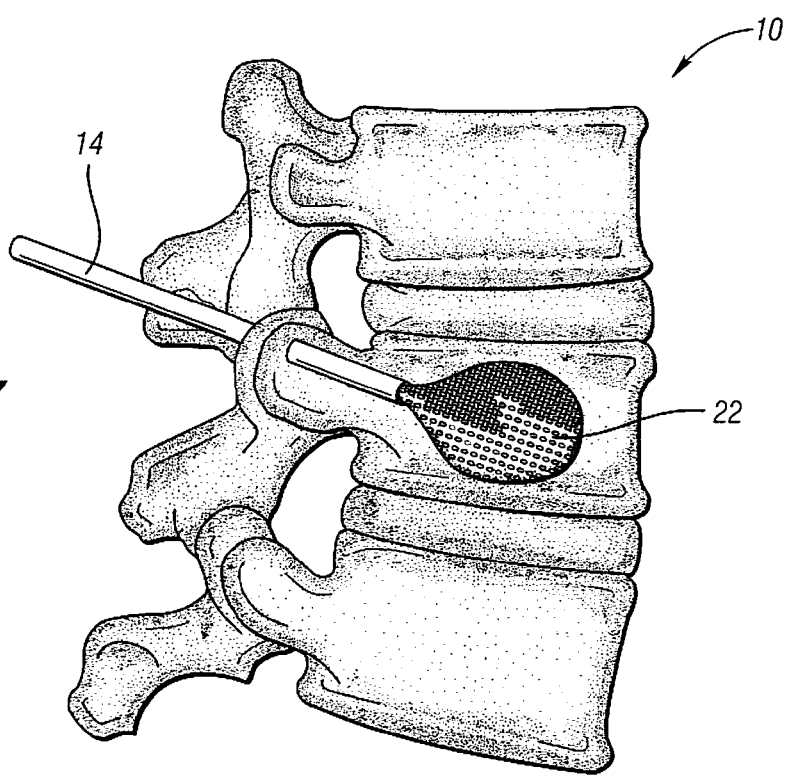
FIG. 4 is a partial side view of another embodiment for stabilizing a collapsed vertebra in accordance with one example of the present invention.

Referring to FIG. 4, at least one other embodiment for stabilizing a collapsed vertebra 12 of a patient is provided. The method includes placing a bone tamp or balloon 22 into the collapsed vertebra 12. The balloon 22 may be placed into the vertebra 12 for example via the needle 14, a catheter or mandrel. The balloon 22 is then filled with the supercooled liquid 16 and sealed. The balloon 22 may be sealed for example by twisting the needle 14 and shearing the corresponding end portion of the balloon 22 or alternatively by applying an adhesive, such as a cyanoacrylate, to the end portion. The filled balloon 22 may be solidified anytime before, during or after sealing the balloon 22.

The balloon may be made of any suitable material used for medical intracorporeal balloon devices. However, a polymer impermeable to body fluid is preferred, especially if the solid structure 20 has any significant solubility in body fluids. PET and PBT are good examples of such preferred polymer materials.

The interventionalist may also assess whether the collapsed vertebra 12 is sufficiently filled with the filled balloon via fluoroscopy. If the collapsed vertebra 12 is not sufficiently filled, an additional balloon may be placed within the collapsed vertebra 12 and the filling, solidifying and sealing steps may be repeated.

Figure 5A:
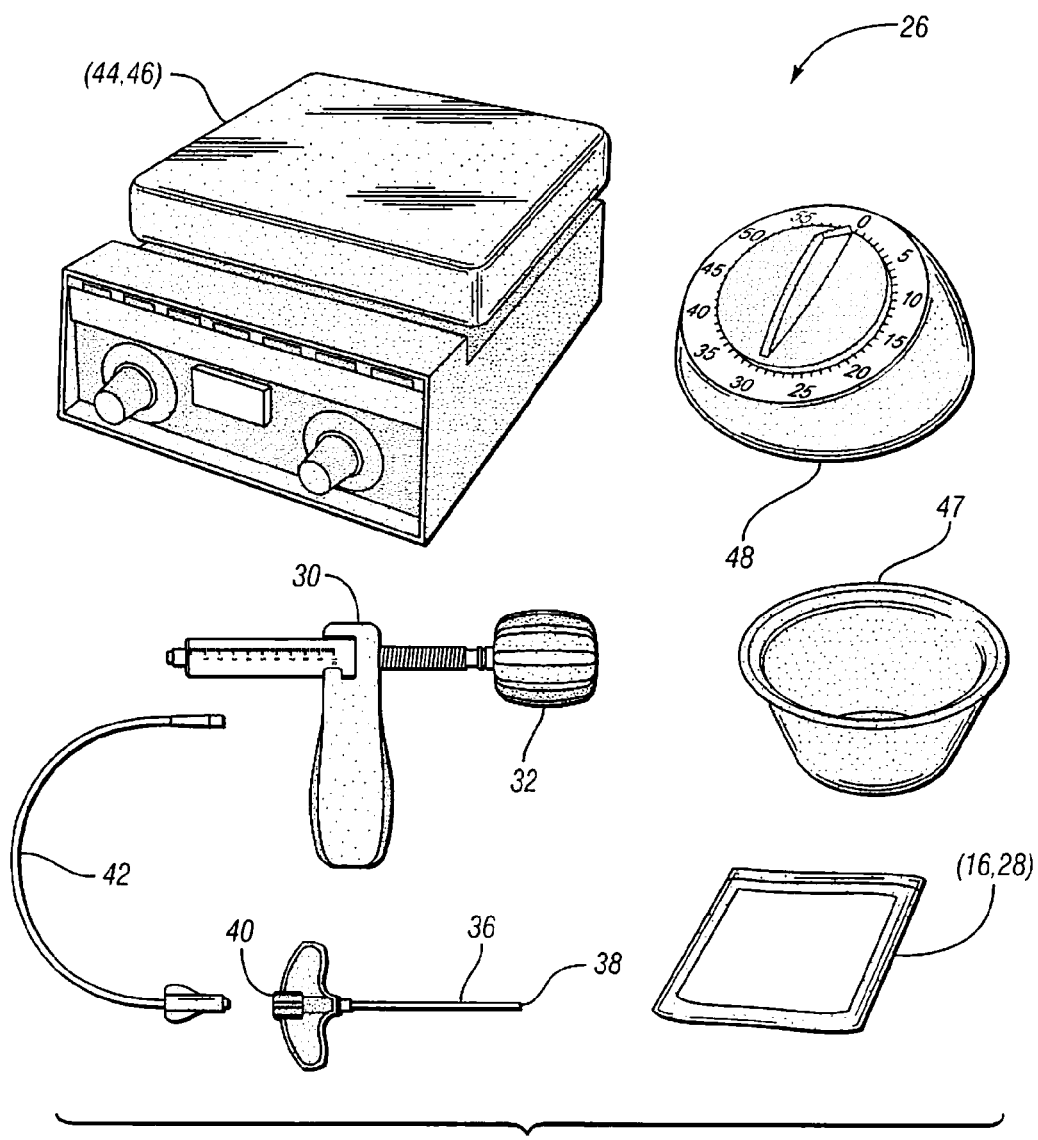
FIG. 5a is a perspective view of an embodiment of a bone cement substitute kit in accordance with one example of the present invention.
Figure 5B:
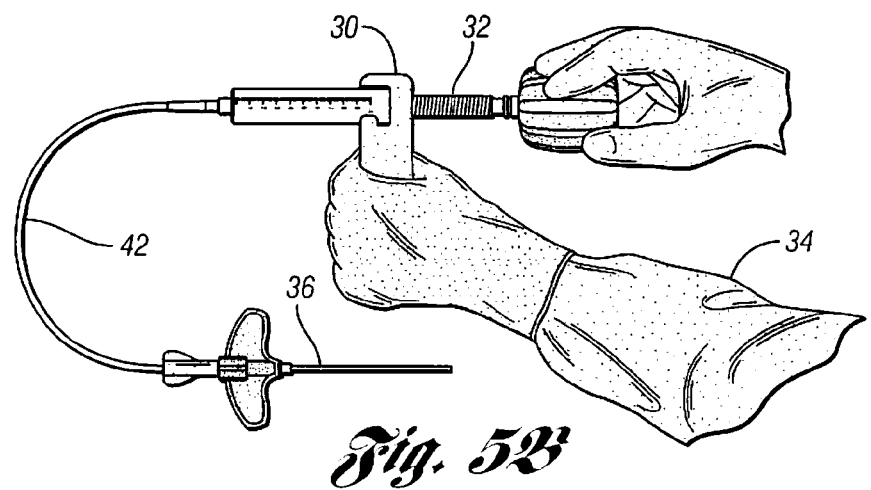
FIG. 5b is a side view of the bone cement substitute kit depicted in FIG. 5a in a partially assembled form.

Referring also to FIGS. 5a and 5b, at least one embodiment of a bone cement substitute kit for stabilizing a collapsed vertebra 12 of a patient is provided. In this embodiment, the kit 26 includes the supercooled liquid 16 or a precursor of the supercooled liquid 16. In one example, the precursor of the supercooled liquid 16 is pre-measured and provided in a sealed package 28. This form of packaging may facilitate shipping and handling of the precursor of the supercooled liquid 16 as well as ensure its purity.

In one embodiment, the precursor of the supercooled liquid 16 includes a plurality of crystals contained in the sealed package 28. An interventionalist 34 may remove one of the crystals from the sealed package 28 to be used as a seed crystal, while using the remaining crystals to prepare the supercooled liquid 16. Alternatively, the kit 26 may include an electrical charge device (not shown) such as for example electrodes coupled to a power supply or an electrical transducer which imparts an electrical charge to the supercooled liquid 16 to form the solid structure 20. Yet another alternative is that the kit 26 may include an energy impulse device (not shown) such as for example an ultrasonic head coupled to a motor or an ultrasonic transducer which provides an energy impulse to the supercooled liquid 16 to form the solid structure 20.

The kit 26 further includes a syringe 30 with a plunger 32. The syringe 30 is for receiving the supercooled liquid 16 and configured so that the interventionalist 34 may actuate the plunger 32 and dispense the supercooled liquid 16 from the syringe 30. In at least one embodiment, the plunger 32 is screw-plunger which the interventionalist 34 actuates by rotating the plunger 32 so that the plunger 32 is advanced through the syringe 32 by corresponding receiving threads (not shown) in the syringe 30. The screw-plunger may provide fast pressure build-up and precise speed control for dispensing the supercooled liquid 16.

The kit 26 further includes a needle 36 configured for fluid communication with the syringe 30 and for advancing the supercooled liquid 16 into the collapsed vertebra 12. The needle 36 may have an end 38 with a bevelled-edged for easy insertion and removal from the collapsed vertebra 12. The other end 40 of the needle 36 may be directly coupled to the syringe 30 or indirectly coupled via tubing 42 which also provides fluid communication between the syringe 30 and the needle 36. The tubing 42 may be flexible to facilitate manoeuvring of the syringe 30 during injection of the supercooled fluid 16 into the vertebra 12.

In one embodiment, the tubing 42 is pressure sensitive and changes colors at higher injection pressures of the supercooled liquid 16. For example, during injection of the supercooled liquid 16 into the collapsed vertebra 12, the tubing 42 changes color because of the increased back pressure created when the collapsed vertebra 12 becomes full with the supercooled liquid 16. The color change signals to the interventionalist 34 that the filling step of the collapsed vertebra 12 is complete.

In another embodiment, the electrical charge devise or the energy impulse device is coupled to the syringe 30. Either device, when activated, initiates nucleation of the supercooled liquid 16 causing solidification to form the solid structure 20 while the needle 36 is still dwelling within the vertebra 12.

The bone cement substitute kit 26 may further comprise a heater 44 for heating the precursor of the supercooled liquid 16 above its melting point. A cooling device 46 may also be provided either integral with the heater 44 or as a stand alone unit. The cooling device 46 is for cooling the heated precursor of the supercooled liquid 16 below the melting point to form the supercooled liquid 16. A container 47 may also be provided for holding the precursor of the supercooled liquid 16 while it is being heated and/or cooled. Additionally, a timer 48 may also be provided for timing the heating and cooling of the precursor of the supercooled liquid 16 to help insure complete transformation to the supercooled liquid 16.

As a person skilled in the art will readily appreciate, the above description is meant as an illustration of implementation of the principles of this invention. This description is not intended to limit the scope or application of this invention in that the invention is susceptible to modification, variation and change, without departing from the spirit of this invention, as defined in the following claims.

The invention claimed is:

1. A method for stabilizing a collapsed vertebra of a patient, the method comprising:
   introducing a supercooled liquid into the collapsed vertebra; and
   solidifying the supercooled liquid to form a structure that supports the collapsed vertebra.

2. The method according to claim 1 wherein the supercooled liquid is microencapsulated within a membrane that is substantially impermeable to body fluids.

3. The method according to claim 1 wherein the supercooled liquid comprises sodium acetate, sodium acetate trihydrate, sodium sulfate, Glauber's salt, organic salt, eutectic salt or a mixture thereof.

4. The method according to claim 1 wherein the supercooled liquid includes reinforcing means for increasing strength of the structure.

5. The method according to claim 1 wherein the supercooled liquid includes a radiopacifier allowing for monitoring the supercooled liquid within the collapsed vertebra during the steps of introducing and solidifying the supercooled liquid.

6. The method according to claim 1 wherein the supercooled liquid includes a thickener for adjusting viscosity of the supercooled liquid.

7. The method according to claim 1 wherein the step of solidifying the supercooled liquid includes introducing a seed crystal to the supercooled liquid.

8. The method according to claim 1 wherein the step of solidifying the supercooled liquid includes applying an electrical charge to the supercooled liquid.

9. The method according to claim 1 where in the step of solidifying the supercooled liquid includes applying an energy impulse to the supercooled liquid.

10. The method according to claim 1 wherein the supercooled liquid forms the structure by crystallization which produces a liquid to solid phase-change of the supercooled liquid.

11. The method according to claim 1 wherein the step of solidifying the supercooled liquid to form the structure occurs within a time of about 60 seconds.

12. The method according to claim 1 wherein the step of introducing the supercooled liquid includes introducing a balloon into the collapsed vertebra and filling the balloon with the supercooled liquid.

13. A method for stabilizing a collapsed vertebra of a patient, the method comprising:
   inserting a needle into the collapsed vertebra;
   introducing a supercooled liquid from the needle and into the collapsed vertebra;
   filling at least a portion of the collapsed vertebra with the supercooled liquid; and
   solidifying the supercooled liquid to form a structure that supports the collapsed vertebra.

14. The method of claim 13 further comprising reviewing the collapsed vertebra via fluoroscopy to determine if the collapsed vertebra is sufficiently filled with the supercooled liquid.

15. The method of claim 13 further comprising placing a balloon into the collapsed vertebra and the step of filling the collapsed vertebra includes filling the balloon with the supercooled liquid.

16. The method of claim 15 further comprising sealing the filled balloon.

17. A method for stabilizing a bone of a patient, the method comprising:
   introducing a supercooled liquid into the interior of the bone; and
   solidifying the supercooled liquid within the bone to form a structure that internally supports the bone.

18. The method of claim 17, wherein the bone has a fracture, and the introducing and the solidifying are at least part of a treatment for the fractured bone.

19. The method of claim 18, wherein the bone is a vertebra, and the fracture is a compression fracture.

20. The method of claim 19, wherein the introducing and the solidifying are at least part of one of a kyphoplasty procedure and a vertebroplasty procedure.

21. The method of claim 17, wherein the supercooled liquid includes a thickener for adjusting viscosity, the thickener being added during the introducing.

22. The method of claim 17, wherein the supercooled liquid includes a thickener for adjusting viscosity, the thickener being premixed with the supercooled liquid prior to the introducing.

23. The method of claim 17, wherein the supercooled liquid includes a thickener for adjusting viscosity, wherein the thickener does not induce premature nucleation of the supercooled liquid.

* * * * *